(12) United States Patent
Heringslack

(10) Patent No.: US 8,130,970 B2
(45) Date of Patent: Mar. 6, 2012

(54) EAR CUP

(75) Inventor: Henrik Heringslack, Varnamo (SE)

(73) Assignee: 3m Innovative Properties Company, St. Paul, MN (US)

( * ) Notice: Subject to any disclaimer, the term of this patent is extended or adjusted under 35 U.S.C. 154(b) by 1163 days.

(21) Appl. No.: 11/912,572

(22) PCT Filed: Apr. 26, 2006

(86) PCT No.: PCT/SE2006/000496
§ 371 (c)(1),
(2), (4) Date: Oct. 25, 2007

(87) PCT Pub. No.: WO2006/118514
PCT Pub. Date: Nov. 9, 2006

(65) Prior Publication Data
US 2009/0279711 A1  Nov. 12, 2009

(30) Foreign Application Priority Data
Apr. 29, 2005 (SE) ........................................ 0500981

(51) Int. Cl.
*H04R 25/00* (2006.01)
(52) U.S. Cl. .......................... 381/71.6; 381/370; 381/371
(58) Field of Classification Search ................. 381/71.6, 381/71.7, 370, 371
See application file for complete search history.

(56) References Cited

U.S. PATENT DOCUMENTS

| | | | |
|---|---|---|---|
| 2,235,372 A | 3/1941 | Kalbitz | |
| 3,087,028 A | 4/1963 | Bonnin | |
| 3,306,991 A | 2/1967 | Wood | |
| 3,394,226 A | 7/1968 | Andrews, Jr. | |
| 3,456,263 A | 7/1969 | Aileo | |
| 3,579,640 A | 2/1970 | Beguin | |
| 3,833,939 A | 9/1974 | Dostourian | |
| 3,869,584 A | 3/1975 | Wilde | |
| 3,890,474 A | 6/1975 | Glicksberg | |
| 3,952,158 A | 4/1976 | Kyle | |
| 4,027,113 A | 5/1977 | Matsumoto | |

(Continued)

FOREIGN PATENT DOCUMENTS

DE  10117704  9/2001

(Continued)

OTHER PUBLICATIONS

International Search Report; PCT/SE2006/000496; Aug. 8, 2006.

*Primary Examiner* — Zandra Smith
*Assistant Examiner* — Paul Patton
(74) *Attorney, Agent, or Firm* — Emily M. Van Vliet

(57) ABSTRACT

An ear cup for a hearing protection unit including an inner cup portion which defines a noise damping space facing towards the user. The ear cup further has an outer cup portion for accommodating electronics and/or a current source. The inner cup portion and the outer cup portion are separated by a partition which is of one piece manufacture with the inner cup portion. The partition is substantially closed, with the exception of an opening in which a fixing portion on a bracket is disposed. The fixing portion (9) has a central channel (15) for the passage of supply conductors to a loudspeaker. The supply conductors have a contact placed on the outside of the partition for connection of the electronics. The bracket also has a baffle plate which extends along the periphery of the loudspeaker.

11 Claims, 4 Drawing Sheets

U.S. PATENT DOCUMENTS

| | | |
|---|---|---|
| 4,064,362 A | 12/1977 | Williams |
| 4,066,849 A | 1/1978 | Chladil, Sr. |
| 4,087,653 A | 5/1978 | Frieder, Jr. |
| 4,302,635 A | 11/1981 | Jacobsen |
| 4,327,257 A | 4/1982 | Schwartz |
| 4,677,678 A | 6/1987 | McCutchen |
| 4,829,571 A | 5/1989 | Kakiuchi |
| 4,833,719 A | 5/1989 | Carme et al. |
| 4,867,149 A | 9/1989 | Falco |
| 4,928,311 A | 5/1990 | Trompler |
| 4,965,836 A | 10/1990 | Andre |
| 4,985,925 A | 1/1991 | Langberg |
| 5,125,032 A | 6/1992 | Meister |
| 5,181,252 A * | 1/1993 | Sapiejewski et al. ......... 381/372 |
| 5,251,263 A | 10/1993 | Andrea |
| 5,402,497 A | 3/1995 | Nishimoto |
| 5,497,427 A * | 3/1996 | Nageno .................... 381/381 |
| 5,519,783 A | 5/1996 | Kumar |
| 5,550,923 A | 8/1996 | Hotvet |
| 5,631,965 A | 5/1997 | Chang |
| 5,675,658 A | 10/1997 | Brittain |
| 6,631,279 B2 | 10/2003 | Rivera |
| 6,704,428 B1 | 3/2004 | Wurtz |
| 6,724,906 B2 | 4/2004 | Naksen |
| 6,728,388 B1 | 4/2004 | Nageno |
| 6,748,087 B1 | 6/2004 | Jones |
| 6,801,629 B2 | 10/2004 | Brimhall |
| 6,965,681 B2 | 11/2005 | Almqvist |
| 6,970,571 B2 | 11/2005 | Knorr |
| 7,099,485 B2 | 8/2006 | Dittli |
| 7,245,735 B2 | 7/2007 | Han |
| 7,308,106 B2 | 12/2007 | Vaudrey |
| 7,327,850 B2 | 2/2008 | Crump |
| 7,391,878 B2 | 6/2008 | Liao |
| 7,664,282 B2 | 2/2010 | Urso |
| 2001/0046304 A1 | 11/2001 | Rast |
| 2002/0001391 A1 | 1/2002 | Darbut |
| 2002/0003889 A1 | 1/2002 | Fischer |
| 2004/0125976 A1 | 7/2004 | Reneker |
| 2004/0125977 A1 | 7/2004 | Hong |
| 2007/0183606 A1 | 8/2007 | Doty |
| 2007/0274529 A1 | 11/2007 | Nordin |
| 2008/0011084 A1 | 1/2008 | Von Dach et al. |
| 2008/0192973 A1 | 8/2008 | Heringslack |
| 2008/0279411 A1 | 11/2008 | Suzuki |
| 2011/0124300 A1 | 5/2011 | Sinai |

FOREIGN PATENT DOCUMENTS

| | | |
|---|---|---|
| EP | 0465971 A2 | 1/1992 |
| EP | 0967592 | 12/1999 |
| EP | 1629808 A1 | 3/2006 |
| FR | 2695302 | 3/1994 |
| GB | 1160431 A | 8/1969 |
| GB | 1289993 A | 9/1972 |
| GB | 2445984 A | 7/2008 |
| WO | WO 87/04065 | 7/1987 |
| WO | WO 91/07153 | 5/1991 |
| WO | WO 96/08004 | 3/1996 |
| WO | WO 97/28742 A1 | 8/1997 |
| WO | WO 02/17838 | 3/2002 |
| WO | WO 03/086124 | 10/2003 |
| WO | WO 2005/051255 | 6/2005 |
| WO | WO 2006/118514 | 11/2006 |
| WO | WO 2008/099137 | 8/2008 |
| WO | WO 2008/113822 | 9/2008 |

* cited by examiner

EAR CUP

TECHNICAL FIELD OF THE INVENTION

The present invention relates to an ear cup for a hearing protection unit with means for sound reproduction via a loudspeaker, comprising: a first cup portion which defines a noise damping space facing towards the user, the first cup portion having, along its periphery, sealing means for abutment against the head of the wearer, and a noise absorbent interiorly in the noise damping space, and a second, outer cup portion for defining a space for accommodating electronics and/or a current source, the noise damping space and the space for accommodating electronics and/or a current source being separated by means of a partition.

BRIEF DISCUSSION OF RELATED ART

As regards ear cups for noise damping, the striving us to make the noise damping volume as great as possible in order also to attain satisfactory results in lower frequency ranges. In such situations when the ear cup is to be provided with means for communication or sound reproduction, a loudspeaker and electronics are required, as well as a current source and a microphone.

It is previously known in the art that both the loudspeaker and associated electronics are disposed interiorly in the ear cup, inside its noise damping space. Such a construction encroaches only a little on the available effective space noise damping space, for which reason the noise damping capability in low frequencies will still be relatively good.

However, the placing of electronics interiorly in the noise damping space entails major problems, since the electronics may rapidly become damaged by moisture formed interiorly in the ear cup.

Designs and constructions are also previously known in the art in which the noise damping volume is smaller and discrete and separated by the intermediary of a partition from a space for accommodating the electronics. In such constructions, it is often the case that the loudspeaker itself is mounted in a large opening in the partition, which causes resultant problems in sealing. Also in such situations where the loudspeaker is disposed interiorly in the noise damping space, openings are required in the partition for screw unions, wiring passages and the like. In such situations as well, sealing problems occur but also problems involving rational mounting and assembly.

BRIEF SUMMARY OF THE INVENTION

By way of the invention, the drawbacks inherent in the prior art technology are obviated or at least greatly reduced. In particular, the invention provides an ear cup configured so that a satisfactory sealing is obtained between the noise damping space and its surroundings, and an extremely simple and rational mounting is achieved. In addition, the present invention realizes an ear cup which is simple and economical in manufacture.

The invention provides an ear cup where the partition is of one piece manufacture with the first cup portion and is substantially closed, that the loudspeaker is secured in a bracket which has a fixing portion which, under sealing, is fixable in an opening in the partition, and that an electric supply conductor to the loudspeaker is included in the fixing portion.

BRIEF DESCRIPTION OF THE DRAWINGS

The present invention will now be described in greater detail hereinbelow, with reference to the accompanying Drawings. In the accompanying Drawings.

DETAILED DESCRIPTION OF THE INVENTION

The ear cup which is the subject matter of the present invention is intended to be included in a hearing protection unit of the type which has two ear cups that are interconnected via a crown stirrup or strap. The crown stirrup or strap extends over the wearer's crown so that both of the ear cups cover the wearer's ears and enclose them.

Use will be made below of directional indications such as forwards, backwards, upwards or downwards. These directional indications refer to a situation where the hearing protection unit is worn in the normal position on a wearer's head with the crown stirrup or strap extending up over the crown of the wearer. Correspondingly, the expressions inwards and outwards, respectively, relate to a direction in towards the wearer's head and away from the wearer's head, respectively.

Figure 1:
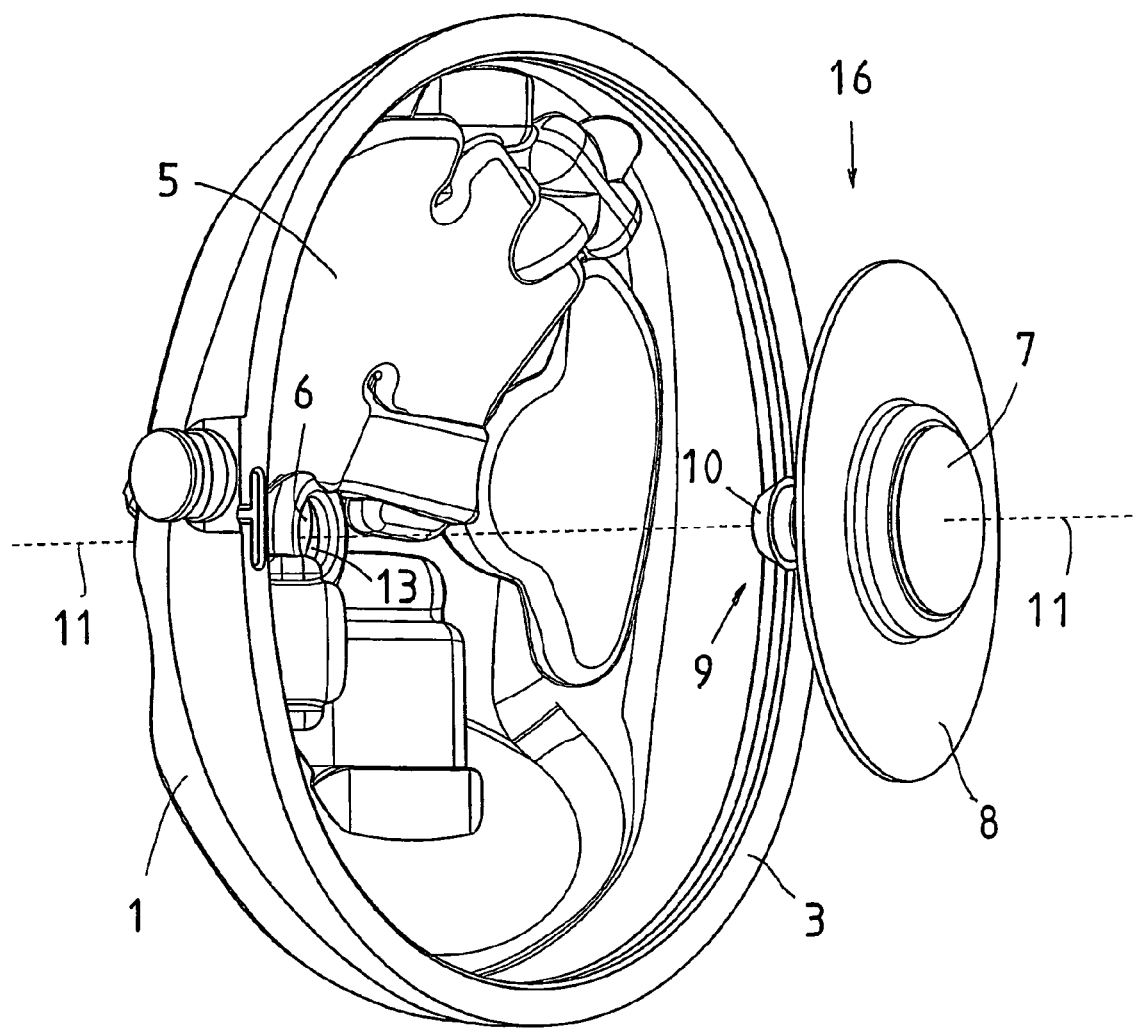
FIG. 1 shows, from the inside and in perspective, the right-hand ear cup included in a hearing protection unit.
Figure 2:
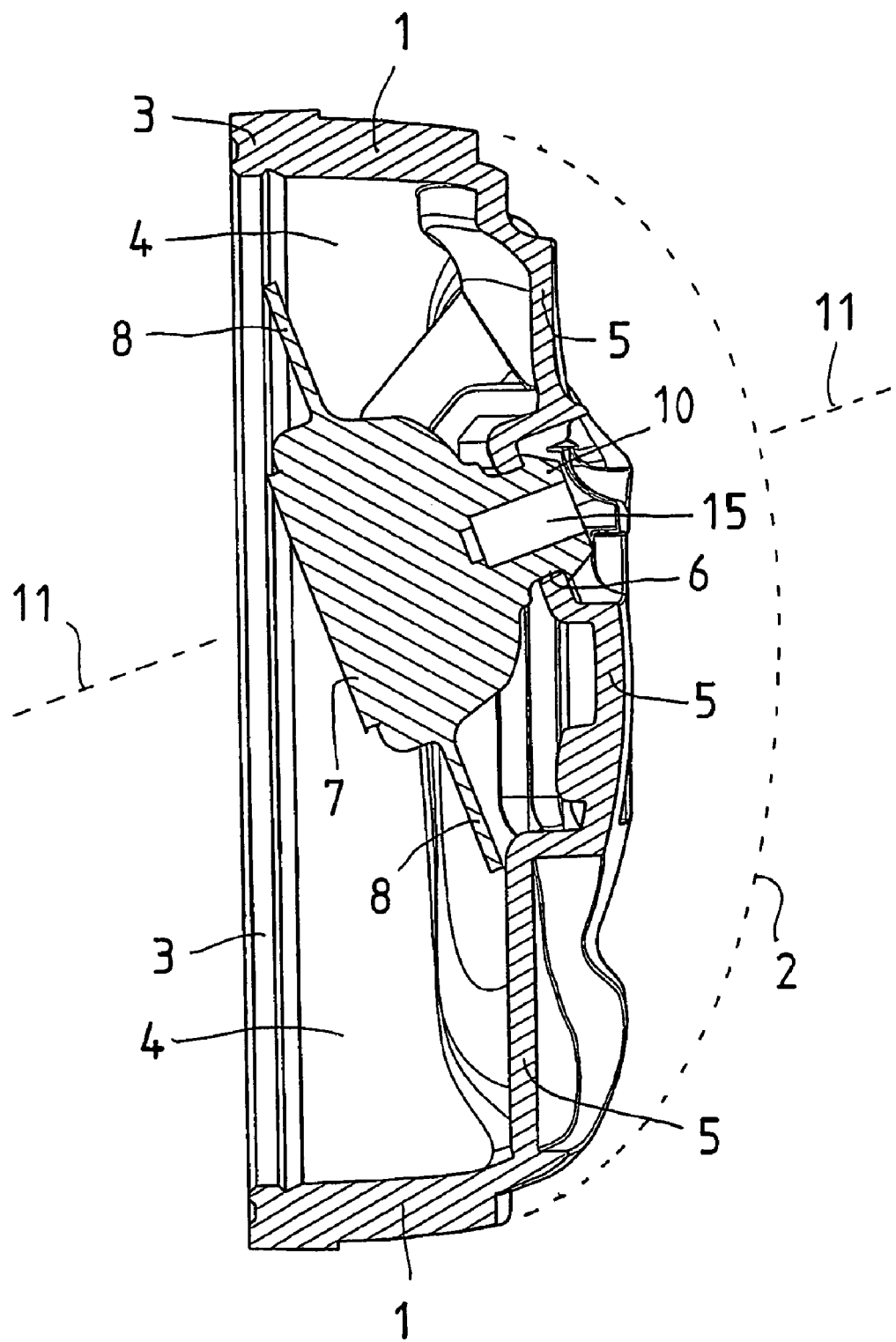
FIG. 2 is a horizontal section seen from above through the ear cup according to FIG. 1, the section lying in the vertical direction at the broken line.

FIGS. 1 and 2 show the right-hand ear cup included in a hearing protection unit, FIG. 1 showing a perspective view seen from the inside of the cup, while FIG. 2 shows a cross section. It will be apparent from the latter Figure that the ear cup has a first, inner portion 1 and a second, outer portion 2. IN such instance, FIG. 2 shows the first or inner portion of the cup in cross section, while the second or outer portion is only intimated by means of broken lines. The first portion 1 of the ear cup has, along its periphery 3 facing towards the wearer's head, sealing means which are not shown on the Drawings, but which are intended to sealingly abut against the wearer's head about the ear. This implies that, between the head of the wearer and interiorly in the first portion 1 of the cup, there is formed a noise damping space 3 in which a noise absorbent is usually disposed.

Outwards, in other words away from the wearer's head, the noise damping space 4 is closed by means of a partition 5 of one piece manufacture with the first portion 1 of the cup, the partition being substantially closed. In the illustrated embodiment, the partition 5 has but a single opening 6, whose purpose will be described in greater detail below. That disclosed above implies in particular that the partition 5 has no separate openings for the passage of conductors, as well as for screw unions, snap catches or the like. All electronics, current source and all connections are thus located on the outside of the partition 5 and interiorly in the outer cup portion. As a result, simple and rational mounting and assembly will be made possible, since soldering can be avoided and no sealing is retroactively required of conductors or other passages.

It will be apparent from FIGS. 1 and 2 that a loudspeaker 7 is disposed in a bracket 16 which has a baffle plate 8, and a fixing portion 9 which is intended under sealing to be fixed in the opening 6 of the partition 5. A supply conductor 19 for the loudspeaker 7 is integrated in the fixing portion 9. In such instance, the supply conductor extends through a sealed, axial channel 15 through the fixing portion. It should be emphasised that the bracket 16 with the loudspeaker 7 and its supply conductor 19 is an integrated, prefabricated unit, where the supply conductor is provided with a connecting device for electric connection on the outside of the partition 5.

Figure 5:
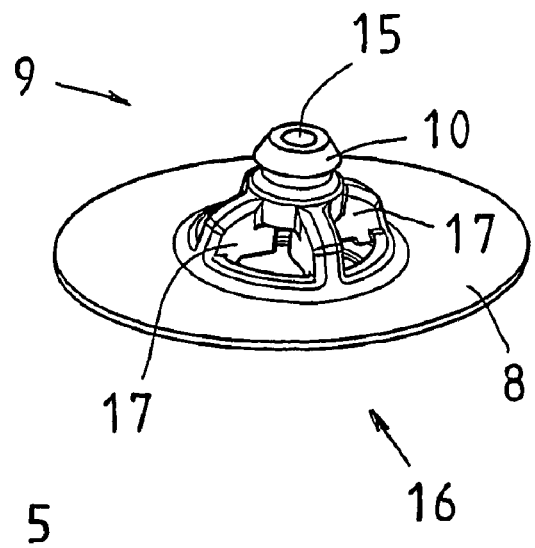
FIG. 5 shows a unit consisting of a loudspeaker, a bracket therefore, with a fixing portion and a baffle plate, all viewed in perspective.
Figure 6:
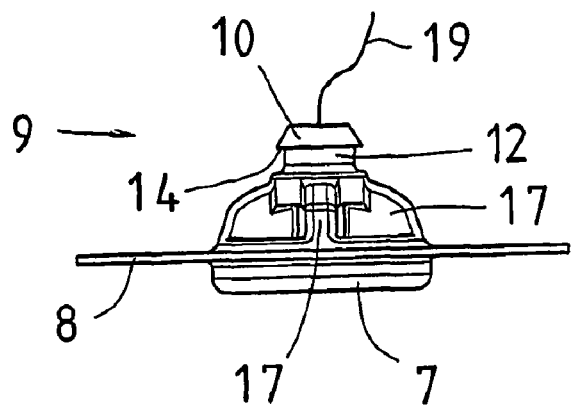
FIG. 6 shows the unit according to FIG. 5 seen in straight aside elevation.

As is apparent from FIGS. 5 and 6, the fixing portion 9 has an entry portion 10 which, in a direction away from the baffle plate 8, tapers or has a conical form. At least the fixing portion 9 and its entry portion 10 are produced from an elastically yieldable material, which implies that the fixing portion, with its entry portion 10, may be passed into the opening 6 in the partition 5 of the inner cup portion 1. Such an insertion takes place along the broke line 11 in FIG. 1 until the entry portion 10 is located on the outside of the partition 5, The entry portion has then snapped into the opening because of its yieldability.

It will further be apparent from FIGS. 5 and 6 that the fixing portion 9 has a circumferential, radial sealing surface 12 for sealing against a circumferential, radial edge surface 13 in the opening 6. It will further be apparent from FIG. 6 that the fixing portion has a circumferential, axial sealing surface 14 for abutment about the opening 6 in the partition 5 on the outside of the partition. Possibly, the fixing portion 9 may have two axial sealing surfaces, one for abutment against each aside of the partition 5.

The broken line 11 shown in FIG. 1 may be seen as a centre axis for the opening 6. The same line is drawn in FIG. 2, also here as a broken line. It will be apparent from FIG. 2 that in two opposing cups, hence a right-hand cup and a left-hand cup, the centre axes of both of the openings of the cups will converge towards one another in a backward direction. This implies that the sound which comes from the loudspeakers 7 will be directed slightly from the front towards the ears of the wearer. This is of advantage from the point of view of good sound reproduction.

The described direction of the loudspeaker 7 also implies that the dimensions of the baffle plate 8 may be maximised without the baffle plate coming into contact with such surfaces as define the noise damping space of the first cup portion 1. As a result, the running distance from the rear side of the loudspeaker 7 around the edge of the baffle plate and up to the front side of the loudspeaker will be maximised, which improves sound reproduction in lower frequency ranges. In this context, it is important that the baffle plate does not on its rear side screen off or possibly more or less seal off a volume that could reduce the size of the effective noise damping space. The periphery of the baffle plate 8 must thus in principle be free in relation to the defining walls of the noise damping space.

Figure 7:
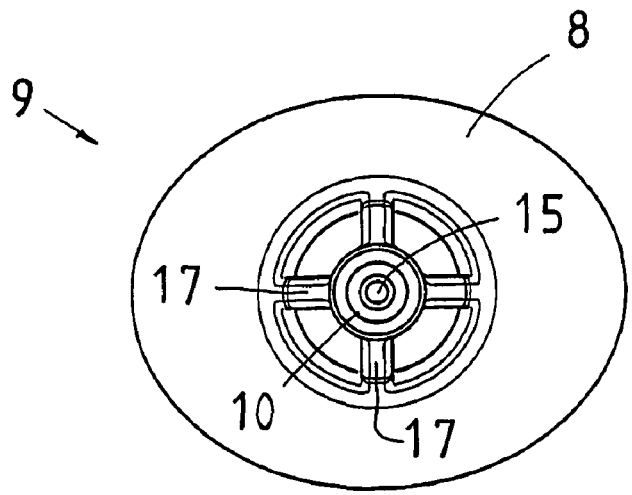
FIG. 7 shows the unit according to FIGS. 5 and 6 in straight plan view seen towards the fixing portion.

It will be apparent from FIGS. 5 and 7 that the fixing portion 9 has a central channel 15 for the passage of supply conductors 19 to the loudspeaker 7 so that a contact placed on the end of these supply conductors may be located on the outside of the partition 5 for connection to the electronics. Naturally, the central channel 15 is sealed around the supply conductors.

As was mentioned above, at least the fixing portion 9 and in particular its entry portion 10 are produced from an elastic, yieldable material. This may suitably also apply to the whole of the bracket 16 in which the loudspeaker 7 is mounted and which also forms the baffle plate 8 along the periphery of the loudspeaker. As was mentioned earlier, the bracket 16 is provided with the fixing portion 9. From this, at least one bracket portion extends up to the periphery of the loudspeaker 7 in order to be secured there. In one practical embodiment, the bracket portion includes a number of arms 17 which, in basket-like fashion, surrounds the loudspeaker 7 proper. The inner ends of the arms 17 merge in an anchorage in which the loudspeaker 7 is secured and from which the baffle plate 8 extends radially outwards. Suitably, the whole of the bracket 16 with the baffle plate 8 is of one piece manufacture from the same elastically yieldable material.

It will be apparent from FIG. 2 that the opening 6 in the cup portion 1 is placed in the front half of the cup. This facilitates and aids the above-described oblique inclination of the loudspeaker 7 and the baffle plate 8.

Figure 4:
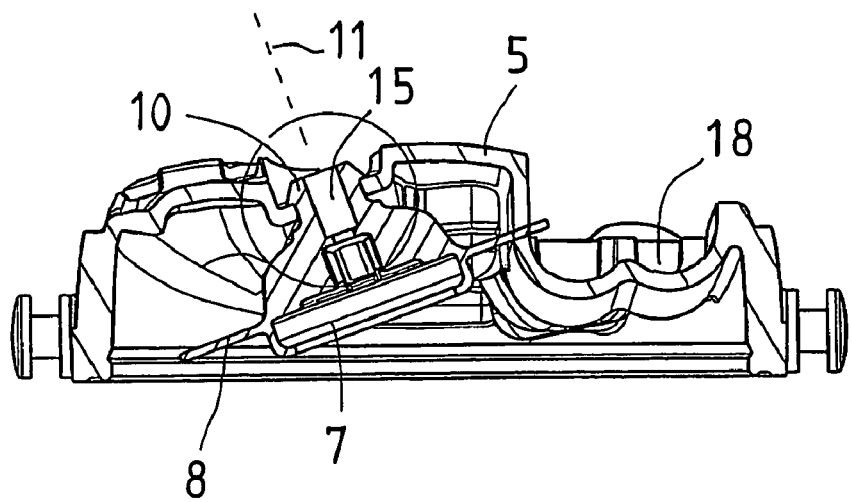
FIG. 4 is a horizontal section through the ear cup according to FIG. 3, the section being shown from beneath.
Figure 3:
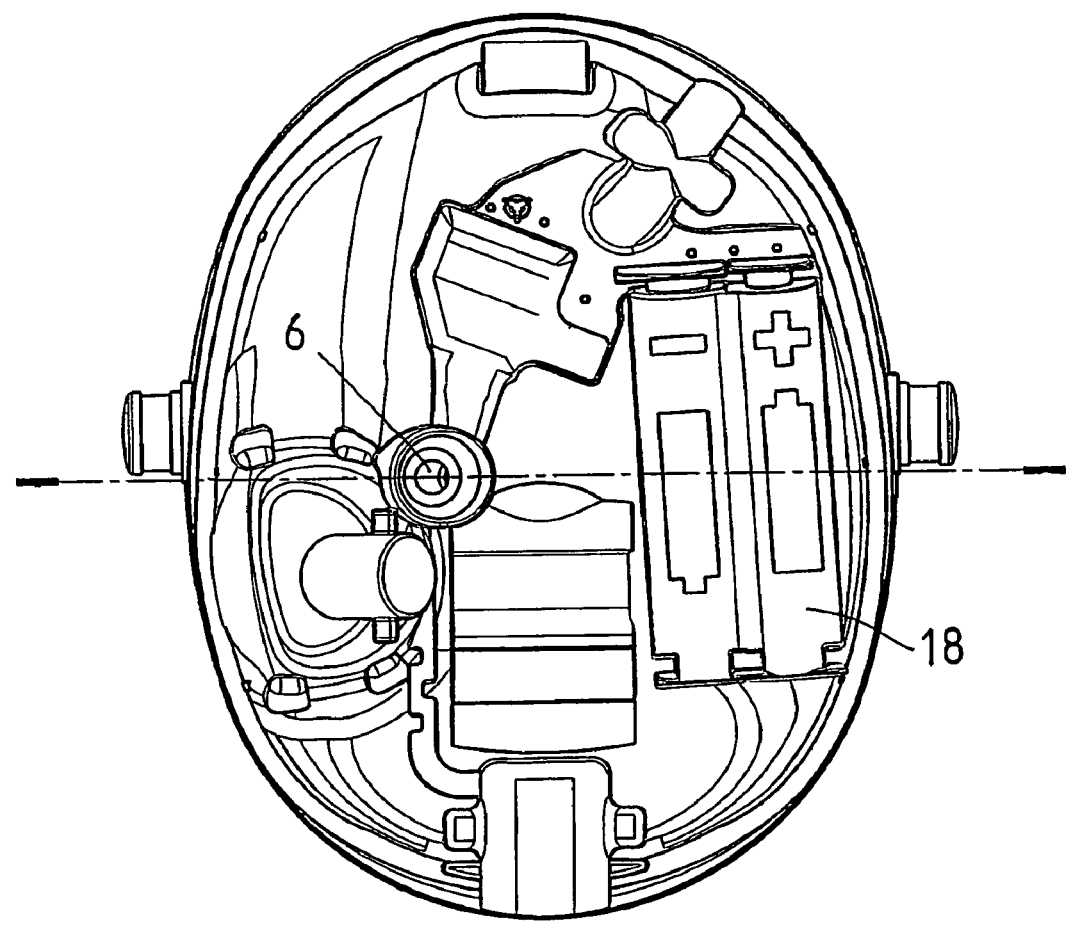
FIG. 3 shows the left-hand ear cup included in a hearing projection unit seen in a plan view from outside.

FIGS. 3 and 4 show the left-hand one of the two ear cups which are included in a hearing protection unit. It will be apparent from FIG. 3 that the outside of this cup has a retainer device 18 for a current source. It will further be apparent that the opening 6 is placed asymmetrically ahead of a vertical centre line to the ear cup.

What is claimed is:

1. An ear cup for a hearing protection unit with means for sound reproduction via a loudspeaker, comprising:
    a first cup portion which defines a noise damping space facing towards a user, the first cup portion having, along a periphery, sealing means for abutment against a head of the wearer, and a noise absorbent interiorly in the noise damping space, and
    a second, outer cup portion for defining a space for accommodating electronics and/or a current source, the noise damping space and the space for accommodating electronics and/or a current source being separated by means of a partition,
    wherein the partition is of one piece manufacture with the first cup portion and is substantially closed, the loudspeaker is secured in a bracket which has a fixing portion produced from an elastic, yieldable material, which, under sealing, is fixable in an opening in the partition, and an electric supply conductor for the loudspeaker is included in the fixing portion.

2. The ear cup as claimed in claim 1, wherein the fixing portion has at least one axial sealing surface for abutment against the partition around the opening.

3. The ear cup as claimed in claim 1, wherein the fixing portion has a radial sealing surface for abutment against a radial edge in the opening of the partition.

4. An ear cup for a hearing protection unit with means for sound reproduction via a loudspeaker, comprising:
    a first cup portion which defines a noise damping space facing towards a user, the first cup portion having, along a periphery, sealing means for abutment against a head of the wearer, and a noise absorbent interiorly in the noise damping space, and
    a second, outer cup portion for defining a space for accommodating electronics and/or a current source, the noise damping space and the space for accommodating electronics and/or a current source being separated by means of a partition,
    wherein the partition is of one piece manufacture with the first cup portion and is substantially closed, the loudspeaker is secured in a bracket which has a fixing portion which, under sealing, is fixable in an opening in the partition, and an electric supply conductor for the loudspeaker is included in the fixing portion;
    wherein the fixing portion has a tapering or conical entry portion for facilitating insertion into the opening of the partition.

5. The ear cup as claimed in claim 1, wherein the bracket has at least one bracket portion which extends from the fixing portion to a periphery of the loudspeaker and is secured there.

6. The ear cup as claimed in claim 5, wherein the bracket portion includes a number of arms which surround the loudspeaker in basket-like fashion.

7. The ear cup as claimed in claim 5, wherein a baffle plate is secured projecting from the periphery of the loudspeaker.

8. The ear cup as claimed in claim 1, wherein the opening in the partition is placed in a front half of the partition.

9. The ear cup as claimed in claim 1, wherein two ear cups included in a hearing protection unit have centre axes for the openings of the partitions, these centre axes converging in a rearward direction.

10. The ear cup as claimed in claim 9, wherein the loudspeakers have baffles which have planes of extent that are transversely directed, substantially at right angles to each respective centre axis.

11. An ear cup for a hearing protection unit with means for sound reproduction via a loudspeaker, comprising:

a first cup portion which defines a noise damping space facing towards a user, the first cup portion having, along a periphery, sealing means for abutment against a head of the wearer, and a noise absorbent interiorly in the noise damping space, and a second, outer cup portion for defining a space for accommodating electronics and/or a current source, the noise damping space and the space for accommodating electronics and/or a current source being separated by means of a partition, wherein the partition is of one piece manufacture with the first cup portion and is substantially closed, the loudspeaker is secured in a bracket which has a fixing portion which, under sealing, is fixable in an opening in the partition, and an electric supply conductor for the loudspeaker is included in the fixing portion;

wherein the supply conductor of the loudspeaker extends through a sealed, axial channel through the fixing portion.

* * * * *

UNITED STATES PATENT AND TRADEMARK OFFICE
CERTIFICATE OF CORRECTION

| | | |
|---|---|---|
| PATENT NO. | : 8,130,970 B2 | Page 1 of 1 |
| APPLICATION NO. | : 11/912572 | |
| DATED | : March 6, 2012 | |
| INVENTOR(S) | : Henrik Heringslack | |

It is certified that error appears in the above-identified patent and that said Letters Patent is hereby corrected as shown below:

ON THE TITLE PAGE:

Item (73) Assignee:
Delete "3m" and insert -- 3M -- therefor.

Item (57) Abstract:
After "portion" delete "(9)".

Item (57) Abstract:
After "channel" delete "(15)".

Signed and Sealed this
Eleventh Day of December, 2012

David J. Kappos
*Director of the United States Patent and Trademark Office*